United States Patent
Rothermel et al.

(10) Patent No.: US 9,821,132 B2
(45) Date of Patent: Nov. 21, 2017

(54) PATIENT INTERFACE DEVICE INCLUDING AN ADJUSTABLE FOREHEAD SUPPORT HAVING A VERTICAL WHEEL DRIVE MECHANISM

(75) Inventors: Justin Edward Rothermel, Monroeville, PA (US); Chad Zediker, Greensbug, PA (US); Robert Earl Hieber, IV, Export, PA (US); Richard Thomas Haibach, Verona, PA (US); Steven Charles Stegman, Gibsonia, PA (US); Karl Herbert Beitzel, Canton, OR (US); Jason Anthony Belton, Norton, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 304 days.

(21) Appl. No.: 14/115,442

(22) PCT Filed: May 9, 2012

(86) PCT No.: PCT/IB2012/052310
§ 371 (c)(1),
(2), (4) Date: Nov. 4, 2013

(87) PCT Pub. No.: WO2012/156867
PCT Pub. Date: Nov. 22, 2012

(65) Prior Publication Data
US 2014/0096775 A1    Apr. 10, 2014

Related U.S. Application Data

(60) Provisional application No. 61/485,798, filed on May 13, 2011.

(51) Int. Cl.
*A61M 16/06* (2006.01)
*A61M 16/00* (2006.01)

(52) U.S. Cl.
CPC .... *A61M 16/0683* (2013.01); *A61M 16/0057* (2013.01); *A61M 16/06* (2013.01); *A61M 16/0655* (2014.02)

(58) Field of Classification Search
CPC .......... A61M 16/0683; A61M 16/0057; A61M 16/0644; A61M 16/0633; A61M 16/06;
(Continued)

(56) References Cited

U.S. PATENT DOCUMENTS

| | | | | |
|---|---|---|---|---|
| 5,752,510 A | * | 5/1998 | Goldstein | ......... A61M 16/0488 128/200.24 |
| 7,735,487 B2 | * | 6/2010 | McAuley | .............. A61M 16/06 128/206.21 |

(Continued)

FOREIGN PATENT DOCUMENTS

| WO | WO2006074517 A1 | 7/2006 |
|---|---|---|
| WO | WO2007021777 A2 | 2/2007 |

(Continued)

*Primary Examiner* — Kari Rodriquez
*Assistant Examiner* — Margaret Luarca
(74) *Attorney, Agent, or Firm* — Michael W. Haas

(57) ABSTRACT

A patient interface device (10) includes a patient sealing assembly (60) including a cushion (70), and a frame member (80) coupled to the cushion, and an adjustable forehead support assembly (200) provided at the distal end (120) of the frame member. The adjustable forehead support assembly includes an adjustment mechanism (202) coupled to a forehead cushion (204), wherein the adjustment mechanism includes a forehead cushion support member (212) having a base portion (216) coupled to the forehead cushion and an vertical/upright rotatable wheel member (214). Rotation of the wheel member causes movement of the frame member and the cushion relative to the forehead cushion.

7 Claims, 3 Drawing Sheets

(58) Field of Classification Search
CPC .......... A61M 16/0622; A61M 16/0627; A61M 16/0638; A61M 16/065; A61M 16/0655
USPC .......................... 128/205.25, 206.24, 207.11
See application file for complete search history.

(56) References Cited

U.S. PATENT DOCUMENTS

| | | | |
|---|---|---|---|
| 8,746,249 B2 * | 6/2014 | Matula, Jr. ............ | A61M 16/06 128/205.25 |
| 2008/0066761 A1 * | 3/2008 | Hodos ................... | A61M 16/06 128/206.28 |
| 2008/0135050 A1 * | 6/2008 | Hitchcock ............. | A61M 16/06 128/207.11 |
| 2010/0108069 A1 | 5/2010 | Chang | |
| 2012/0090617 A1 * | 4/2012 | Matula, Jr. ............ | A61M 16/06 128/206.21 |

FOREIGN PATENT DOCUMENTS

| | | | |
|---|---|---|---|
| WO | WO2007143793 | A1 | 12/2007 |
| WO | WO2010133218 | A2 | 11/2010 |

* cited by examiner

PATIENT INTERFACE DEVICE INCLUDING AN ADJUSTABLE FOREHEAD SUPPORT HAVING A VERTICAL WHEEL DRIVE MECHANISM

CROSS-REFERENCE TO RELATED APPLICATIONS

This patent application claims the priority benefit under 35 U.S.C. 371 of international patent application no. PCT/IB2012/052310, filed May 9, 2012, which claims the priority benefit under 35 U.S.C. §119(e) of U.S. Provisional Application No. 61/485,798 filed on May 13, 2011, the contents of which are herein incorporated by reference.

BACKGROUND OF THE INVENTION

1. Field of the Invention

The present invention relates to patient interface devices for transporting a gas to and/or from an airway of a user, and in particular, to a patient interface device including a mechanism for adjusting a forehead support of the patient interface device that includes a vertical wheel drive mechanism.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Because such patient interface devices are typically worn for an extended period of time, it is important for the headgear to maintain the mask component of the device in a tight enough seal against the patient's face without discomfort. One area where fit and comfort is often a concern is the bridge of the patient's nose, as most patient interface devices will apply a pressure to this area. If this pressure is not able to be managed effectively, either or both of a poor fit or patient discomfort will result, thereby limiting the effectiveness of the device.

SUMMARY OF THE INVENTION

Accordingly, it is an object of the present invention to provide a patient interface device that overcomes the shortcomings of conventional patient interface devices. This object is achieved according to one embodiment of the present invention by providing a patient interface device that includes a selectively adjustable forehead support assembly that allows for simple and convenient management of the nose bridge pressure that is applied by the patient interface device.

In one embodiment, a patient interface device is provided that includes a patient sealing assembly adapted to communicate a flow of breathing gas within an airway of a patient, the patient sealing assembly including a cushion and a frame member coupled to the cushion. The device also includes an adjustable forehead support assembly provided at the distal end of the frame member. The adjustable forehead support assembly includes an adjustment mechanism coupled to a forehead cushion, wherein the adjustment mechanism includes a forehead cushion support member and a rotatable wheel member. The forehead cushion support member has a base portion coupled to the forehead cushion, wherein the base portion has a first axis structured to extend in a first direction from a left side of the patient's forehead to a right side of the patient's forehead, and a second axis normal to the first axis and structured to extend in a second direction from a lower portion of the patient's forehead to an upper portion of the patient's forehead when the patient interface device is donned by the patient. In addition, the wheel member is oriented in an upright condition with respect to the base portion such that the wheel member is rotatable about a rotation axis that is parallel to the first direction and normal to the second direction and within a rotational plane that is parallel to the second direction and normal to the first direction, wherein rotation of the wheel member causes movement of the frame member and the cushion relative to the forehead cushion.

In another embodiment, a method of adjusting the patient interface device just described is provided that includes rotating the upright rotatable wheel member in a first rotation direction about a rotation axis that is parallel to the first direction and normal to the second direction and within a rotational plane that is parallel to the second direction and normal to the first direction to move the frame member toward the forehead cushion, and rotating the upright rotatable wheel member in a second rotation direction opposite the first rotation direction to move the frame member away from the forehead cushion.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
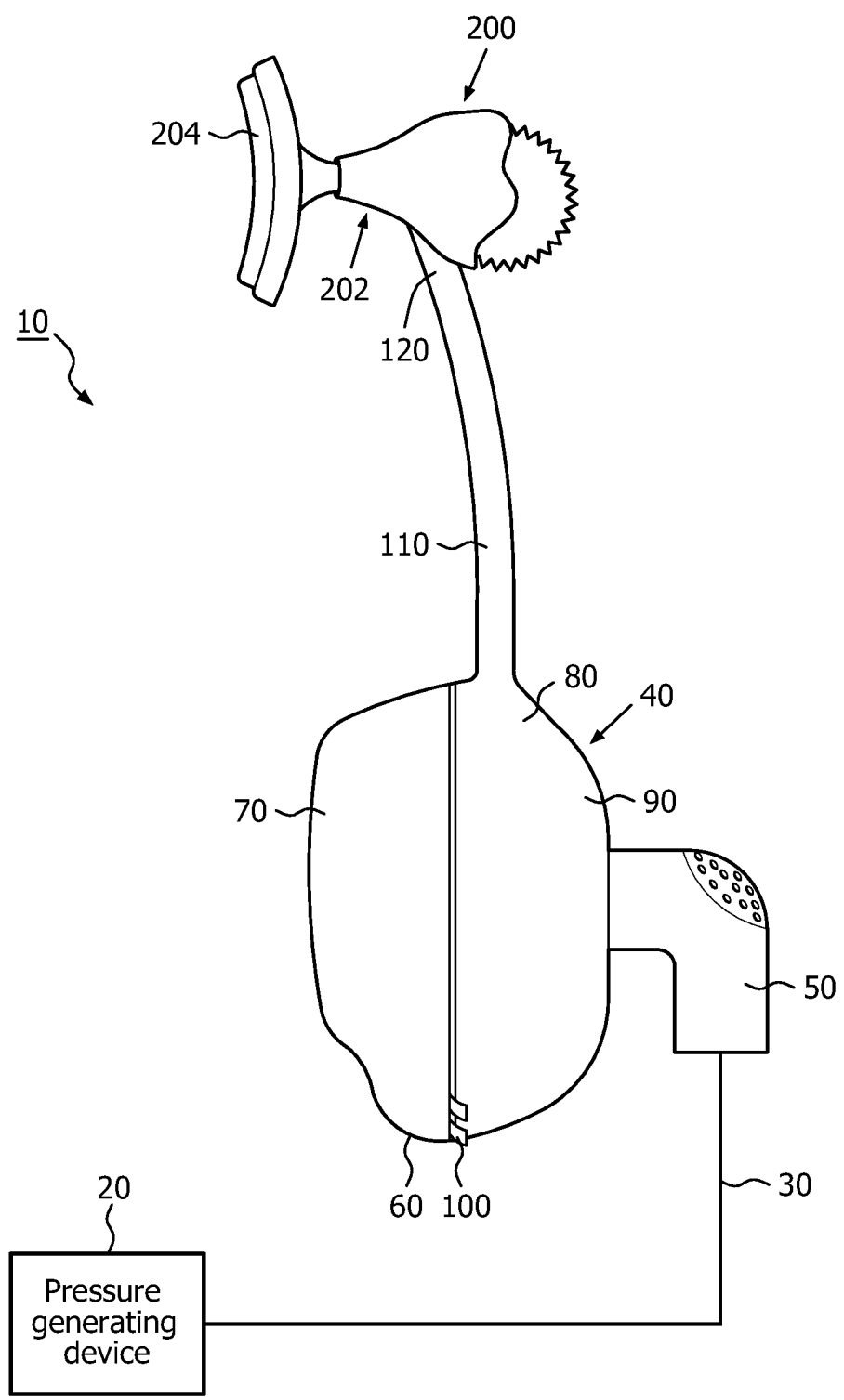
FIG. 1 is a schematic diagram of a system adapted to provide a regimen of respiratory therapy to a patient according to one exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 10 adapted to provide a regimen of respiratory therapy to a patient according to one exemplary embodiment is generally shown in FIG. 1. System 10 includes a pressure generating device 20, a delivery conduit 30, and a patient interface device 40 having a fluid coupling conduit 50. Pressure generating device 20 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 30 is structured to communicate the flow of breathing gas from pressure generating device 20 to patient interface device 40 through fluid coupling conduit 50, which in the illustrated embodiment is an elbow connector. Delivery conduit 30 and patient interface device 40 are often collectively referred to as a patient circuit.

Patient interface device 40 includes a patient sealing assembly 60, which in the illustrated embodiment is a nasal mask. However, other types of patient sealing assemblies, such as, without limitation, a nasal/oral mask or a nasal cushion, which facilitate the delivery of the flow of breathing gas to the airway of a patient may be substituted for patient sealing assembly 60 while remaining within the scope of the present invention. Patient sealing assembly 60 includes a cushion 70 coupled to a frame member 80. In the illustrated embodiment, cushion 70 is defined from a unitary piece of soft, flexible, cushiony, elastomeric material, such as, without limitation, silicone, an appropriately soft thermoplastic elastomer, a closed cell foam, or any combination of such materials. Of course, a wide variety of other configurations for the cushion are contemplated by the present invention, including multi-component cushions, and cushions with other features, such as inflatable bladders, color changing materials, imbedded sensors, and any other conventional components or materials contemplated for use with a cushion.

In the illustrated embodiment, frame member 80 is made of a rigid or semi-rigid material, such as, without limitation, an injection molded thermoplastic or silicone, and includes a faceplate portion 90 to which cushion 70 is fluidly attached. An opening in faceplate portion 90, to which fluid coupling conduit 50 is coupled, allows the flow of breathing gas from pressure generating device 20 to be communicated to an interior space defined by cushion 70, and then to the airway of a patient. In an alternative embodiment, cushion 70 may be supported by and received through an orifice in frame member 80 so that fluid coupling conduit 50 can be directly connected to cushion 70 rather than to a faceplate portion. In addition, in the exemplary embodiment, faceplate portion 90 includes first and second socket type connecting members 100 for receiving a ball connector of a respective strap of a headgear component (not shown) to secure patient interface device 8 to the patient's head.

Frame member 80 also includes an elongated connecting member 110 having a distal end 120 that is connected to an adjustable forehead support assembly 200 of patient interface device 40. Adjustable forehead support assembly 200 includes an adjustment mechanism 202 that is coupled to a forehead cushion 204, which in the exemplary embodiment, is made of a material that is similar to the material of cushion 70. As described in detail herein, adjustment mechanism 200 provides a mechanism for selectively adjusting the force applied to the bridge of the nose of a patient by an apex portion of cushion 70 by varying the position of connecting member 110, and in particular distal end 120 thereof, with respect to forehead cushion 204.

Figure 2:
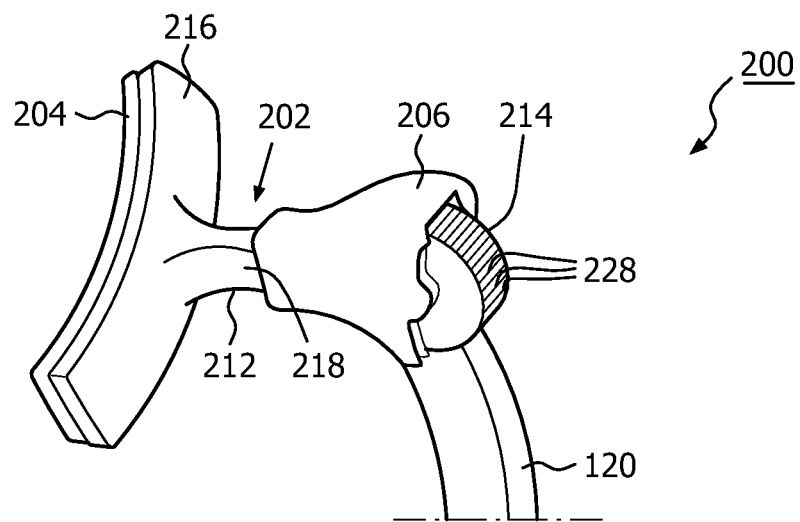
FIG. 2 is an isometric view.
Figure 3:
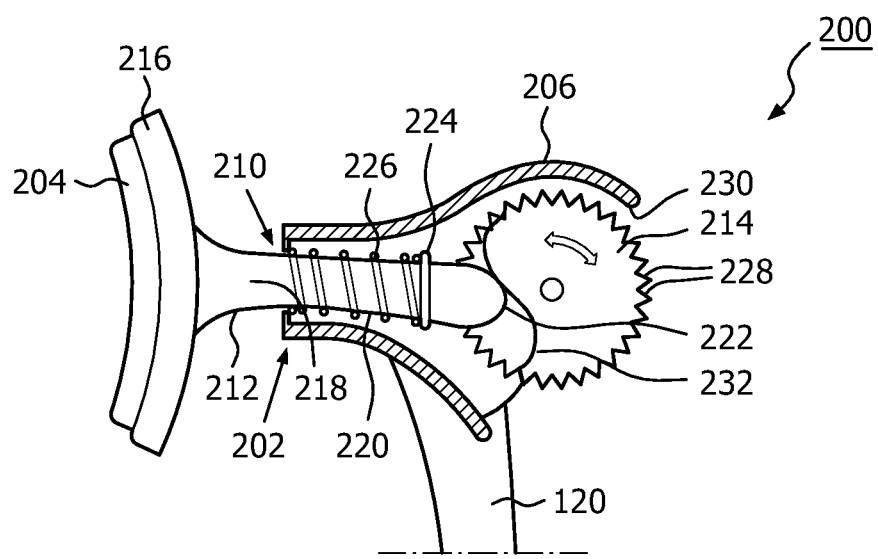
FIG. 3 is a side view in partial cross-section of an adjustable forehead support assembly according forming a part of a patient interface device of the system of FIG. 1.

FIG. 2 is an isometric view and FIG. 3 is a side view in partial cross-section of adjustable forehead support assembly 200. Adjustment mechanism 202 includes a housing portion 206 coupled to the distal end 120 of frame member 80. In the illustrated embodiment, housing portion 206 is formed as an integral part of frame member 80, although in alternative embodiments it may also be formed separately and attached to frame member 80 by a suitable mechanism such as an adhesive. Adjustment mechanism 202 also includes a linear translation assembly 210 (described in greater detail below) partially received and housed within housing portion 206.

Linear translation assembly 210 includes a forehead cushion support member 212 and a rotatable cam wheel member 214. Forehead cushion support member 212 includes a base portion 216 to which forehead cushion 204 is attached, and an elongated post member 218 extending from base portion 216. As can best be seen in FIG. 2, base portion 218 has a first axis structured to extend from the left side of the patient's forehead to the right side of the patient's forehead when patient interface device 40 is donned by the patient. Base portion 218 also has a second axis that is normal to the first axis and structured to extend from the lower portion of the patient's forehead to the upper portion of the patient's forehead when patient interface device 40 is donned by the patient.

In the exemplary embodiment, post member 218 includes a main body 220 having a rounded distal end 222 and a flanged outer edge 224. In addition, a spring member 226 is wrapped around a portion of main body 220 below flanged outer edge 224 as shown in FIG. 3.

Cam wheel member 214 is received in and extends outwardly from a front end of housing portion 206. As seen in FIGS. 1-3, wheel member 214 is oriented in a vertical/upright condition with respect to base portion 218 such that wheel member 214 is rotatable about a rotation axis that is parallel to the direction of the first axis of base portion 218 and normal to the direction of the second axis of base portion 218 described above. As such, wheel member 214 is rotatable within a rotational plane that is parallel to the direction of the second axis and normal to the direction of the first axis. In other words, the center of cam wheel member 214 about which it rotates lies in the same plane (a central plane) as the longitudinal axis of post member 218 such that the rotational plane of cam wheel member 214 just described is parallel to and coextensive with the central plane. In the exemplary embodiment, cam wheel member 214 is a generally disk shaped member having detents 228 provided along the outer circumference thereof.

In addition, housing portion 206 includes a pawl member 230 that is structured to be received in the notches in between detents 228 to control the rotation of cam wheel member 214 so that it is not able to simply spin freely. Cam wheel member 214 also includes a generally S-shaped cam portion 232 that is structured to interact with rounded distal end 222 of post member 218. In particular, by rotating cam wheel member 214, spring member 226 may be selectively compressed or allowed to expand depending on the position of rounded distal end 222 along cam portion 232. This action will cause the position of housing portion 206 and frame member 208 relative to forehead cushion support member 212 and forehead cushion 204 (which will be at a fixed position on the patient's head) to be linearly adjusted. This linear adjustment action allows for selective adjustment of the force that is applied to the bridge of the patient's nose by the apex portion of cushion 70 because varying the position of connecting member 110 as just described will cause the apex portion of cushion 70 to rotate toward and away from the patient's nose.

Figure 4:
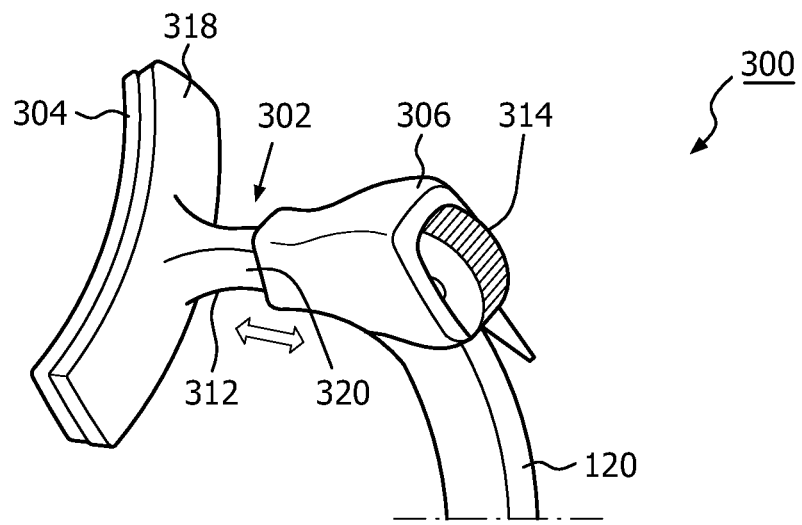
FIG. 4 is an isometric view and FIG. 5 is a side view in partial cross-section of an adjustable forehead support assembly according to an alternative embodiment of the present invention.
Figure 5:
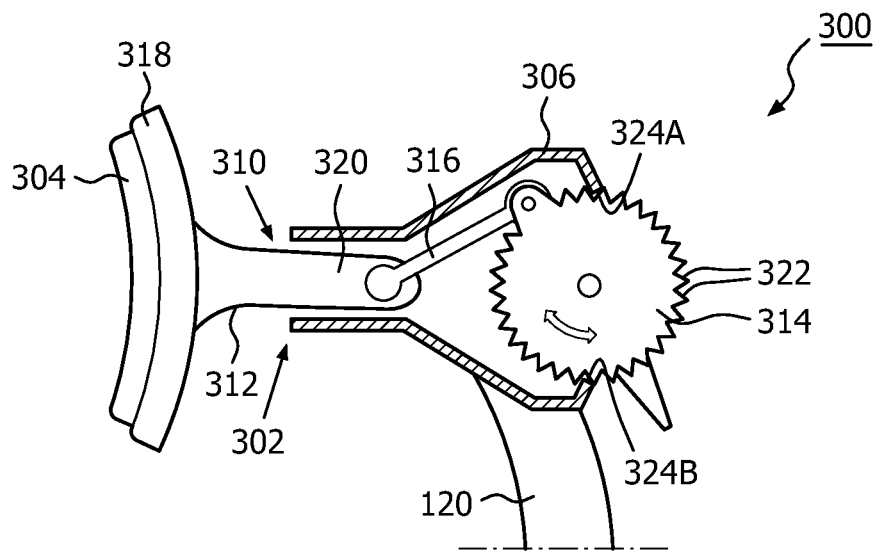

FIG. 4 is an isometric view and FIG. 5 is a side view in partial cross-section of an adjustable forehead support assembly 300 according to an alternative embodiment of the present invention. Adjustable forehead support assembly 300 may be substituted for adjustable forehead support assembly 200 of patient interface device 40 in system 10. Adjustable forehead support assembly 300 includes an adjustment mechanism 302 that is coupled to a forehead cushion 304.

Adjustment mechanism 302 includes a housing portion 306 coupled to the distal end 120 of frame member 80. In the illustrated embodiment, housing portion 306 is formed as an integral part of frame member 80, although in alternative embodiments it may also be formed separately and attached to frame member 110 by a suitable mechanism such as an adhesive. Adjustment mechanism 302 also includes a linear translation assembly 310 (described in greater detail below) partially received and housed within housing portion 306.

Linear translation assembly 310 includes a forehead cushion support member 312, a rotatable wheel member 314, and a linkage arm 316 provided in between forehead cushion support member 312 and rotatable wheel member 314. Forehead cushion support member 312 includes a base portion 318 to which forehead cushion 304 is attached, and an elongated post member 320 extending from base portion 318. As can best be seen in FIG. 4, base portion 318, like base portion 218, has a first axis structured to extend from the left side of the patient's forehead to the right side of the patient's forehead when patient interface device 40 is donned by the patient. Base portion 318 also has a second axis that is normal to the first axis and structured to extend from the lower portion of the patient's forehead to the upper portion of the patient's forehead when patient interface device 40 is donned by the patient. A first end of linkage arm 316 is rotatably coupled to post member 320 and a second, opposite end of linkage arm 316 is rotatably coupled to rotatable wheel member 314.

Wheel member 314 is received in and extends outwardly from a front end of housing portion 306. As seen in FIGS. 4 and 5, wheel member 314 is oriented in a vertical/upright condition with respect to base portion 318 such that wheel member 314 is rotatable about a rotation axis that is parallel to the direction of the first axis of base portion 318 and normal to the direction of the second axis of base portion 318 described above. As such, wheel member 314 is rotatable within a rotational plane that is parallel to the direction of the second axis and normal to the direction of the first axis. In other words, the center of wheel member 314 about which it rotates lies in the same plane (a central plane) as the longitudinal axis of post member 318 such that the rotational plane of wheel member 314 just described is parallel to and coextensive with the central plane. In the exemplary embodiment, wheel member 314 has detents 322 provided along the outer circumference thereof.

Housing portion 306 includes pawl members 324A, 324B that are structured to be received in the notches in between detents 228 to control the rotation of wheel member 314 so that it is not able to simply spin freely. By rotating wheel member 314, linkage arm 316 is moved back and forth within housing portion 306, which in turn causes post member 320 to move linearly back and forth within housing portion 306. This action will cause the position of housing portion 306 and frame member 308 relative to forehead cushion support member 312 and forehead cushion 304 (which will be at a fixed position on the patient's head) to be linearly adjusted, thereby allowing for selective adjustment of the force that is applied to the bridge of the patient's nose as described elsewhere herein.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
   a patient sealing assembly adapted to communicate a flow of breathing gas within an airway of a patient, the patient sealing assembly including a cushion and a frame member coupled to the cushion; and
   an adjustable forehead support assembly provided at a distal end of the frame member, the adjustable forehead support assembly including an adjustment mechanism coupled to a forehead cushion, the adjustment mechanism comprising:
   (i) a forehead cushion support member having a base portion coupled to the forehead cushion, wherein the base portion has a first axis structured to extend in a first direction from a left side of the patient's forehead to a right side of the patient's forehead and a second axis normal to the first axis and structured to extend in a second direction from a lower portion of the patient's forehead to an upper portion of the patient's forehead when the patient interface device is donned by the patient, wherein the forehead cushion support member further includes an elongated post member extending from the base portion; and
   (ii) a rotatable wheel member coupled to the base portion, wherein the wheel member is oriented with respect to the base portion such that the wheel member is rotatable about a rotation axis that is parallel to the first direction and normal to the second direction and within a rotational plane that is parallel to the second direction and normal to the first direction, wherein the wheel member includes a cam portion that is structured to engage a distal end of the elongated post member, wherein rotation of the wheel member causes the cam member to exert a direct force against the distal end of the elongated post member and thereby cause relative movement between the elongated post member and the wheel member and between the base member and the distal end of the frame member, and wherein movement of the distal end of the frame member relative to the base member causes movement of the frame member and the cushion relative to the forehead cushion, wherein the elongated post member includes a main body, wherein the distal end of the elongated post member is rounded, and wherein the cam portion is a generally S-shaped cam portion.

2. The patient interface device according to claim 1, wherein when the patient interface device is donned by the patient, movement of the frame member and the cushion relative to the forehead cushion will adjust a force applied to a bridge of a nose of the patient by an apex portion of the cushion by causing the cushion to pivot relative to the patient's nose.

3. The patient interface device according to claim 1, wherein the adjustment mechanism includes a housing, wherein the wheel member is provided at last partially within the housing, and wherein the elongated post member is received within the housing, wherein rotation of the wheel member causes relative movement between the elongated post member and the housing in a direction along a longitudinal axis of the elongated post member, and wherein movement of the housing relative to the elongated post member causes movement of the frame member and the cushion relative to the forehead cushion.

4. The patient interface device according to claim 1, wherein the adjustment mechanism further includes a spring member wrapped around a portion of the main body, wherein rotation of the wheel member in a first rotation direction compresses the spring member and rotation of the wheel member in a second rotation direction allows the spring member to expand.

5. The patient interface device according to claim 1, wherein the adjustment mechanism includes a housing, wherein the wheel member is provided at last partially within the housing, wherein the wheel member is a generally disk shaped member having detents provided along an outer circumference thereof, wherein the housing includes a pawl member that is structured to cooperate with the detents to control the rotation of the wheel member.

6. A method of adjusting a patient interface device, the patient interface device including a cushion, a frame member coupled to the cushion, a forehead cushion and a forehead cushion support member having a base portion coupled to the forehead cushion, wherein the base portion has a first axis structured to extend in a first direction from a left side of the patient's forehead to a right side of the patient's forehead and a second axis normal to the first axis and structured to extend in a second direction from a lower portion of the patient's forehead to an upper portion of the patient's forehead when the patient interface device is donned by the patient, the method comprising:
   rotating a rotatable wheel member coupled to the base portion in a first rotation direction about a rotation axis that is parallel to the first direction and normal to the second direction and within a rotational plane that is parallel to the second direction and normal to the first direction to move the frame member toward the forehead cushion; and
   rotating the upright rotatable wheel member in a second rotation direction opposite the first rotation direction to move the frame member away from the forehead cushion, wherein the forehead cushion support member includes an elongated post member extending from the base portion, wherein the wheel member includes a cam portion that is structured to engage a distal end of the elongated post member, and wherein the rotating steps cause the cam member to exert a direct force against the distal end of the elongated post member and thereby cause relative movement between the elongated post member and the wheel member wherein the elongated post member includes a main body, wherein the distal end of the elongated post member is rounded, and wherein the cam portion is a generally S-shaped cam portion.

7. The method according to claim 6, wherein the adjustment mechanism further includes a spring member wrapped around a portion of the main body, wherein the rotating the wheel member in the first rotation direction compresses the spring member and the rotating the wheel member in the second rotation direction allows the spring member to expand.

* * * * *